(12) United States Patent
Hanshew, Jr. et al.

(10) Patent No.: US 7,052,717 B2
(45) Date of Patent: *May 30, 2006

(54) STORAGE STABLE THYROXINE ACTIVE DRUG FORMULATIONS AND METHODS FOR THEIR PRODUCTION

(75) Inventors: Dwight D. Hanshew, Jr., Morgantown, WV (US); David John Wargo, Pittsburgh, PA (US)

(73) Assignee: Mylan Pharmaceuticals Inc., Morgantown, WV (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/441,259

(22) Filed: May 20, 2003

(65) Prior Publication Data

US 2004/0013725 A1 Jan. 22, 2004

Related U.S. Application Data

(63) Continuation of application No. 09/987,160, filed on Nov. 13, 2001, now abandoned.

(51) Int. Cl.
*A61K 9/20* (2006.01)

(52) U.S. Cl. ...................... 424/464; 424/465

(58) Field of Classification Search ............... 424/464, 424/465
See application file for complete search history.

(56) References Cited

U.S. PATENT DOCUMENTS

| | | | |
|---|---|---|---|
| 3,946,109 A * | 3/1976 | Kolb | ......................... 424/538 |
| 4,415,547 A | 11/1983 | Yu et al. | |
| 4,666,703 A | 5/1987 | Kopf | |
| 4,910,023 A | 3/1990 | Botzolakis et al. | |
| 5,004,613 A | 4/1991 | Radebaugh et al. | |
| 5,032,405 A | 7/1991 | Huang et al. | |
| 5,073,380 A | 12/1991 | Babu et al. | |
| 5,200,193 A | 4/1993 | Radebaugh et al. | |
| 5,202,128 A | 4/1993 | Morella et al. | |
| 5,225,202 A | 7/1993 | Hodges et al. | |
| 5,225,204 A | 7/1993 | Chen et al. | |
| 5,248,505 A | 9/1993 | Garwin | |
| 5,330,766 A | 7/1994 | Morella et al. | |
| 5,378,474 A | 1/1995 | Morella et al. | |
| 5,456,851 A | 10/1995 | Liu et al. | |
| 5,462,747 A | 10/1995 | Radebaugh et al. | |
| 5,490,990 A | 2/1996 | Grabowski et al. | |
| 5,543,155 A | 8/1996 | Fekete et al. | |
| 5,571,840 A | 11/1996 | Mayor et al. | |
| 5,585,115 A | 12/1996 | Sherwood et al. | |
| 5,635,209 A | 6/1997 | Groenewoud et al. | |
| 5,681,583 A | 10/1997 | Conte et al. | |
| 5,725,883 A | 3/1998 | Staniforth et al. | |
| 5,725,884 A | 3/1998 | Sherwood et al. | |
| 5,741,524 A | 4/1998 | Staniforth et al. | |
| 5,747,068 A | 5/1998 | Mendizabal | |
| 5,753,254 A | 5/1998 | Khan et al. | |
| 5,780,057 A | 7/1998 | Conte et al. | |
| 5,800,834 A | 9/1998 | Spireas et al. | |
| 5,856,359 A | 1/1999 | Fischer et al. | |
| 5,858,412 A | 1/1999 | Staniforth et al. | |
| 5,866,166 A | 2/1999 | Staniforth et al. | |
| 5,948,438 A | 9/1999 | Staniforth et al. | |
| 5,948,926 A | 9/1999 | Takeo et al. | |
| 5,951,989 A | 9/1999 | Heymann | |
| 5,955,105 A | 9/1999 | Mitra et al. | |
| 6,056,975 A | 5/2000 | Mitra et al. | |
| 6,190,696 B1 | 2/2001 | Groenewoud | |
| 6,372,255 B1 | 4/2002 | Saslawski et al. | |
| 6,399,101 B1 | 6/2002 | Frontanes et al. | |
| 6,458,842 B1 * | 10/2002 | Dickinson et al. | ........... 514/567 |
| 6,488,961 B1 * | 12/2002 | Robinson et al. | ........... 424/466 |
| 6,491,946 B1 * | 12/2002 | Schreder et al. | ........... 424/465 |
| 6,555,581 B1 * | 4/2003 | Franz et al. | ............... 514/567 |
| 6,645,526 B1 * | 11/2003 | Hanshew et al. | ........... 424/465 |
| 6,646,007 B1 * | 11/2003 | Schreder et al. | ............ 514/567 |
| 6,649,186 B1 * | 11/2003 | Robinson et al. | ........... 424/466 |
| 6,852,688 B1 * | 2/2005 | Grant | ............................ 514/8 |
| 6,855,333 B1 * | 2/2005 | Spireas | ....................... 424/452 |
| 2002/0044968 A1 | 4/2002 | van Lengerich | |
| 2002/0077364 A1 | 6/2002 | Murari et al. | |
| 2003/0050344 A1 | 3/2003 | Garavani et al. | |
| 2003/0099698 A1 | 5/2003 | Hanshew, Jr. et al. | |
| 2003/0099699 A1 | 5/2003 | Hanshew et al. | |

(Continued)

FOREIGN PATENT DOCUMENTS

JP 2002284679 A 10/2002

(Continued)

OTHER PUBLICATIONS

V. Das Gupta et al., "Effect of Excipients on the Stability of Levothyroxine Sodium Tablets," *J. Clin. Pharm. & Therap.* 15: 331-336 (1990).

(Continued)

*Primary Examiner*—Sreeni Padmanabhan
*Assistant Examiner*—Marina Lamm
(74) *Attorney, Agent, or Firm*—Rothwell, Figg, Ernst & Manbeck pc

(57) ABSTRACT

This invention provides a storage-stable dosage form of a thyroxine active drug composition which exhibits an improved stability. The formulation contains a thyroxine active drug substance and an antioxidant, and, optionally, additional pharmaceutically accepted excipients. Levothyroxine sodium is the preferred active drug substance, butylated hydroxyanisole is the preferred antioxidant. Additional preferred excipients include, for example, microcrystalline cellulose, sucrose, mannitol, crospovidone, magnesium stearate, colloidal silicon dioxide, and sodium lauryl sulfate.

21 Claims, 1 Drawing Sheet

U.S. PATENT DOCUMENTS

| | | |
|---|---|---|
| 2003/0119911 A1 | 6/2003 | Franz et al. |
| 2003/0165564 A1 | 9/2003 | Franz et al. |
| 2003/0171436 A1 | 9/2003 | Franz et al. |
| 2003/0175337 A1 | 9/2003 | Franz et al. |
| 2003/0180353 A1 | 9/2003 | Franz et al. |
| 2003/0180356 A1 | 9/2003 | Franz et al. |
| 2003/0181524 A1 | 9/2003 | Franz et al. |
| 2003/0185885 A1 | 10/2003 | Franz et al. |
| 2003/0190349 A1 | 10/2003 | Franz et al. |
| 2003/0190350 A1 | 10/2003 | Franz et al. |
| 2003/0190359 A1 | 10/2003 | Franz et al. |
| 2003/0191185 A1 | 10/2003 | Franz et al. |
| 2003/0194436 A1 | 10/2003 | Franz et al. |
| 2003/0194437 A1 | 10/2003 | Franz et al. |
| 2003/0195253 A1 | 10/2003 | Franz et al. |
| 2003/0195254 A1 | 10/2003 | Franz et al. |
| 2003/0198667 A1 | 10/2003 | Franz et al. |
| 2003/0198668 A1 | 10/2003 | Franz et al. |
| 2003/0198671 A1 | 10/2003 | Franz et al. |
| 2003/0198672 A1 | 10/2003 | Franz et al. |
| 2003/0199585 A1 | 10/2003 | Franz et al. |
| 2003/0199586 A1 | 10/2003 | Franz et al. |
| 2003/0199587 A1 | 10/2003 | Franz et al. |
| 2003/0199588 A1 | 10/2003 | Franz et al. |
| 2003/0203967 A1 | 10/2003 | Franz et al. |
| 2003/0203968 A1 | 10/2003 | Franz et al. |
| 2003/0224047 A1 | 12/2003 | Franz et al. |
| 2004/0043066 A1 | 3/2004 | Franz et al. |

FOREIGN PATENT DOCUMENTS

| | | |
|---|---|---|
| WO | WO 95/20955 A1 | 8/1995 |
| WO | WO 99/33448 A1 * | 7/1999 |
| WO | WO 99/63969 A2 | 12/1999 |
| WO | WO 01/13936 A1 | 3/2001 |
| WO | WO 01/80822 A2 | 11/2001 |
| WO | WO 02/28364 A2 | 4/2002 |
| WO | WO 02/28364 A3 | 4/2002 |
| WO | WO 02/28365 A2 | 4/2002 |
| WO | WO 02/28365 A3 | 4/2002 |
| WO | WO 02/064093 A2 | 8/2002 |
| WO | WO 02/067854 A2 | 9/2002 |
| WO | WO 03/013441 A2 | 2/2003 |
| WO | WO 03/028624 A2 | 4/2003 |
| WO | WO 03/061557 A2 | 7/2003 |
| WO | WO 03/070217 A1 | 8/2003 |

OTHER PUBLICATIONS

Steven L Richheimer et al., "Stability-Indicating Assay, Dissolution, and Content Uniformity of Sodium Levothyroxine in Tablets," *J. Pharm. Sci* 72(11): 349-51(1983).

"Levothyroxine Loses Potency With Age," *JAMA* 255(14): 1881-82 (1986).

Chong Min Won, "Kinetics of Degradation of Levothyroxine in Aqueous Solution and in Solid State," *Pharm. Research* 9(1):131-37 (1992).

* cited by examiner

STORAGE STABLE THYROXINE ACTIVE DRUG FORMULATIONS AND METHODS FOR THEIR PRODUCTION

This is a continuation of prior application Ser. No. 09/987,160, filed Nov. 13, 2001 now abandoned.

BACKGROUND OF THE INVENTION

1. Field of the Invention

The invention relates generally to the field of medicinal formulations, and more particularly to methods of preparing storage stable pharmaceutical compositions in unit dosage form of levothyroxine sodium with increased shelf life and compositions made by these methods.

2. Description of the Background Art

Thyroxine active drugs are known for both therapeutic and prophylactic treatment of thyroid disorders. For example, levothyroxine sodium is prescribed for thyroid hormone replacement therapy in cases of reduced or absent thyroid function in e.g., ailments such as myxedema, cretinism and obesity. See, for example, Post and Warren in *Analytical Profiles of Drug Substances*, Vol. 5, Florey (ed.); Academic Press, New York (1976), pp. 226–281. Levothyroxine sodium is quite unstable, hygroscopic and degrades rapidly when subjected to high humidity, light or high temperature. See, for example, Won, *Pharm. Res.* 9(1): 131–137, 1992. Because of the chemicophysical properties of the drug, formulations of levothyroxine sodium have extremely short stability duration, worsened under conditions of high humidity and temperature. Tablets may decompose approximately 1 percent per month. Gupta et. al., *J. Clin. Pharm. Ther.* 15:331–335, 1990. The stability problem has been so widespread that some drug companies marketing levothyroxine sodium tablets have been forced to recall various batches due to lack of stability.

Formulations containing levothyroxine sodium have been known in the art since the late 1950s. There have been recent attempts to develop more stable dosage formulations of levothyroxine sodium. For example, U.S. Pat. No. 5,635,209 discloses levothyroxine sodium in combination with potassium iodide as part of a stabilizing excipient. In the manufacture of this formulation, levothyroxine sodium was first mixed with microcrystalline cellulose, and then added to a dried granulation of potassium iodide and microcrystalline cellulose. The formulation purportedly provided increased active drug potency over a three month period in comparison to then commercially available formulations.

U.S. Pat. No. 5,225,204 discloses a complex of levothyroxine sodium and a cellulose, polyvinylpyrrolidone or Poloxamer. The formulation may be prepared by dissolving the drug complex in a polar organic solvent, adding a cellulose carrier to the liquid, and drying the resulting mixture to obtain a complex of levothyroxine sodium and polyvinylpyrrolidone or Poloxamer adsorbed on the cellulose carrier.

Although purportedly increasing the stability of the formulation, the deposition onto cellulose may have resulted in some increased stability due to improved content uniformity. Tests of such combinations yielded stability results at best equal to commercially available preparations such as those described in U.S. Pat. No. 5,955,105, and in some cases substantially worse.

The inventors of this stabilized composition teach one of skill in the art away from the use of carbohydrates in levothyroxine sodium formulations, stating that instability of the dosage form was the result of an interaction between the active drug substance and carbohydrate excipients.

The inventors of U.S. Pat. No. 5,955,105 also teach that the instability of thyroxine drugs is due to an interaction between the drug and the excipient. These inventors incorporated into the formulation a soluble glucose polymer designed to eliminate the interaction between the drug and other excipients contained in the final blend.

Because of degradation of the active ingredient in currently available formulations of levothyroxine sodium, new methods of formulating solid dosage forms of this drug would be highly desirable. Although different methods for producing a formulation stable enough to meet requirements for shelf-life have been attempted, no method has been entirely successful. There is, then, a great need for new formulations of thyroxine active drugs with increased stability and shelf life.

SUMMARY OF THE INVENTION

The present invention relates to methods and compositions which substantially increase the stability of levothyroxine sodium and other thyroxine active drugs. This invention prevents the decreases in effective dosage which plague prior art thyroxine active drug formulations and substantially increases shelf life. The compositions include an active thyroxine drug with an antioxidant and, optionally, an alditol and a saccharide. Other optional ingredients in the composition include but are not limited to pharmaceutically acceptable excipients such as cellulose polymers or carbohydrates, disintegrants, lubricants and glidants.

Accordingly, the present invention provides a storage stable oral pharmaceutical composition which comprises a therapeutically effective amount of a thyroxine active drug and an amount of an antioxidant sufficient to inhibit oxidative degradation of the thyroxine drug. The preferred thyroxine active drug is levothyroxine sodium. Preferred antioxidants include butylated hydroxyanisole. Compositions which further comprise a stabilizing amount of an alditol, preferably mannitol, are also provided by this invention. In another embodiment, the invention provides compositions which further comprise a stabilizing amount of a saccharide, preferably a disaccharide such as sucrose. In yet another embodiment, compositions of the invention comprise at least one further pharmaceutical excipient, such as a carbohydrate, a starch or a modified starch, for example microcrystalline cellulose.

In yet a further embodiment, this invention provides storage stable oral pharmaceutical compositions in unit dosage form comprising the compositions discussed above, and particularly a storage stable oral dosage form composition which comprises levothyroxine sodium, butylated hydroxyanisole, mannitol, sucrose, and optionally further comprises microcrystalline cellulose, polyvinylpyrrolidone, crospovidone, magnesium stearate, sodium lauryl sulfate, and colloidal silicon dioxide. The invention preferably provides such storage stable oral dosage forms in the form of tablets.

A preferred embodiment of the invention encompasses a storage stable oral pharmaceutical composition which comprises a therapeutically effective amount of levothyroxine sodium; about 0.01% by weight butylated hydroxyanisole; about 58% by weight mannitol; about 14% by weight sucrose; about 25% by weight microcrystalline cellulose; about 1.5% by weight polyvinylpyrrolidone; about 1.4% by weight magnesium stearate; about 0.3% by weight colloidal silicon dioxide; and about 0.1% by weight sodium lauryl sulfate.

Another preferred embodiment of the invention encompasses a storage stable oral pharmaceutical composition which comprises a therapeutically effective amount of levothyroxine sodium; about 0.01% by weight butylated hydroxyanisole; about 39% by weight mannitol; about 23% by weight sucrose; about 28% by weight microcrystalline cellulose; about 1.5% by weight polyvinylpyrrolidone; about 6% by weight crospovidone; about 2% by weight magnesium stearate; about 0.3% by weight colloidal silicon dioxide; and about 0.1% by weight sodium lauryl sulfate.

DETAILED DESCRIPTION OF THE INVENTION

Figure 1:
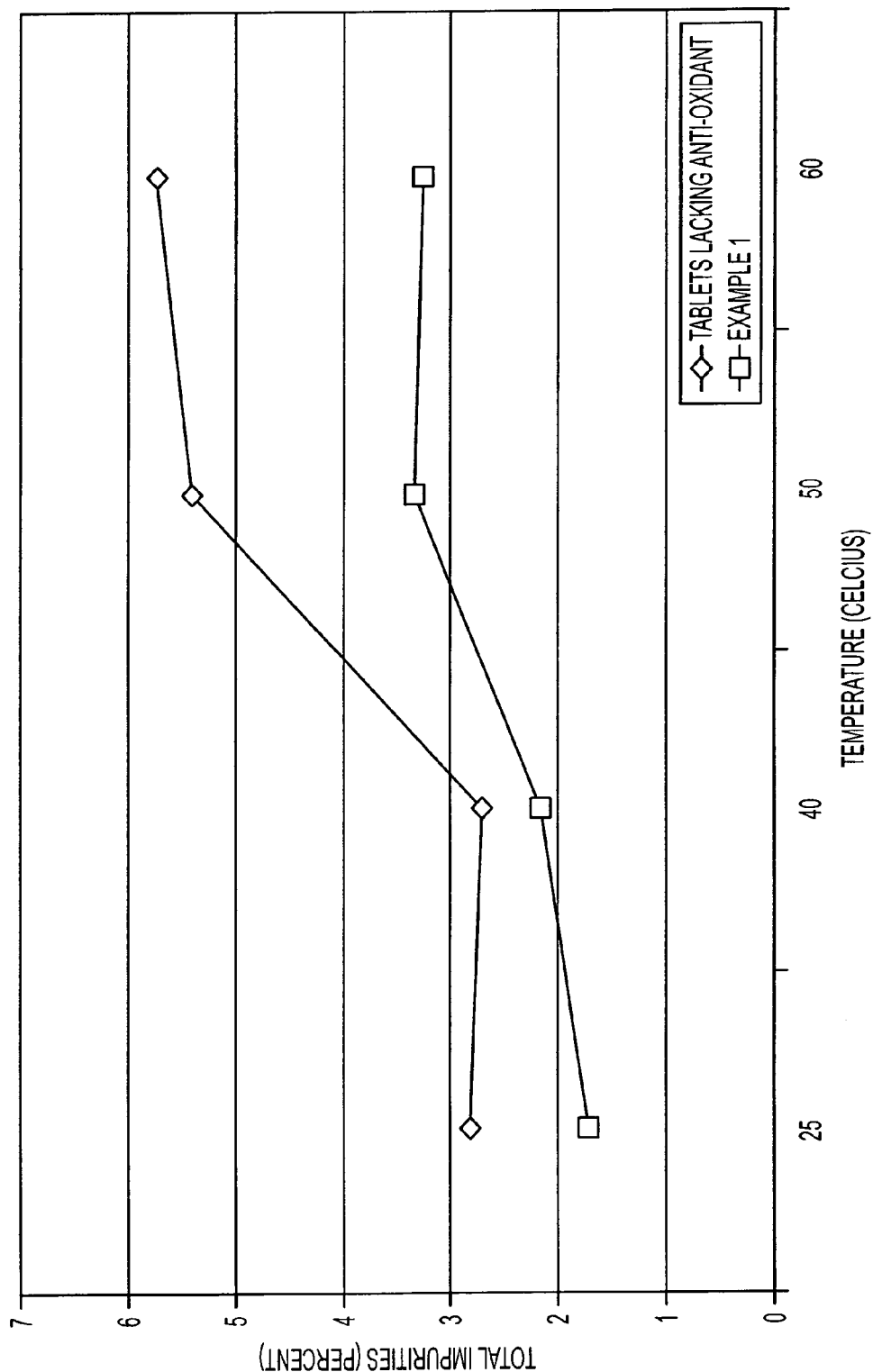
FIG. 1 is a graphic illustration of the stability data generated for storage of tablets made with an antioxidant according to the present invention (Example 1) and made without an antioxidant.

The present invention relates to storage stable granulation intermediates and oral pharmaceutical compositions in unit dosage form of a thyroxine active drug and methods by which they are produced. The methods involve a granulation intermediate containing an antioxidant, the thyroxine active drug substance, an alditol, and a monosaccharide or disaccharide to provide a formulation with a synergistic increase of stability of both the granulation intermediates and the final oral dosage forms prepared from these granulation intermediates. Thus, the present invention provides a stable dosage form in which the dosage of thyroxine active drug is maintained at a predictable level for a longer period of time.

Formulations of levothyroxine with greatly increased resistance to degradation can be produced by providing excipients which reduce or eliminate oxidative degradation of the active substance. Although the prior art indicates that reaction between levothyroxine sodium and certain carbohydrate, monosaccharide or disaccharide excipients is responsible for the poor stability of the drug, the present inventive formulation achieves surprisingly stable levothyroxine dosage forms using these previously disfavored excipients. Additionally, preferred formulations are maintained at a pH of less than about 10.

The methods and formulations of this invention take advantage of the discovery that including an antioxidant results in a surprisingly stable levothyroxine sodium composition. This invention can be used to produce stable formulations of any natural or synthetic thyroid hormone replacement drug. Therefore, although the following description and example refer to compositions and methods using levothyroxine sodium, the invention is understood to encompass other thyroid hormone medications of the general formula

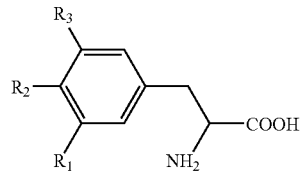

wherein $R_1$ and $R_3$ may be the same or different and are selected from hydrogen; halogen; alkyl; aryl; cycloalkyl; heterocycloalkyl; amide; alcohol; acid; ester; ether; acyl; alkenyl; and alkynyl; wherein $R_2$ is

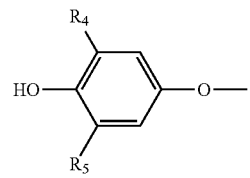

and wherein $R_4$ and $R_5$ may be the same or different and are selected from hydrogen; halogen; alkyl; aryl; cycloalkyl; heterocycloalkyl; amide; alcohol; acid; ester; ether; acyl; alkenyl; and alkynyl. The medication can be in the form of a free acid, a free base, an organic salt, an inorganic salt, or a hydrate. Liothyronine is an example of a drug encompassed by the above-mentioned general formula.

According to this invention, stabilized pharmaceutical compositions are produced by blending the active ingredient with an antioxidant, and optionally an alditol and a saccharide such as a monosaccharide or disaccharide to form a granulation intermediate. Addition of any additional pharmaceutical excipients, diluents or granulation aids is optional. Generally, further pharmaceutical excipients are added to produce final oral dosage forms such as tablets or capsules.

Formulations according to this invention are made according to the following general steps. Those of skill in the art are aware of equivalent methods and variations which produce the same general result. Therefore, the general instructions, and the example which follows should not be considered to be strictly limiting. The active thyroxine ingredient, for example, levothyroxine sodium, is blended with diluents to form a pre-blend for ease of handling. An antioxidant is incorporated into the pre-blended materials to produce a granulation intermediate. Diluents such as an alditol and/or a saccharide, in combination with an antioxidant, are believed to synergistically increase the stability of the granulation intermediate and formulations produced using it. Preferred granulation intermediates are produced by making a wet granulation of the active ingredient with an antioxidant such as butylated hydroxyanisole, an alditol such as mannitol, a saccharide such as sucrose and a granulation aid such as microcrystalline cellulose. Preferably, the active ingredient is blended first with the alditol, sucrose is then added and the material is blended again. The antioxidant is then incorporated into the mixture. According to the invention, further excipients such as microcrystalline cellulose (also polyvinylpyrrolidone as binder) may also be incorporated into the granulation, but need not be added until the active ingredient is intimately mixed with the alditol and/or the sucrose. Therefore, the microcrystalline cellulose or other diluent functions as a granulation aid and compression enhancer (for tablet or capsule formulations) and not as a specific carrier for the thyroxine active drug.

In preferred embodiments, the wet granulation is dried, milled and optionally further blended. The granulation intermediate then may be stored or directly mixed with further ingredients to form a composition suitable for compression into tablets, filling into capsules or dissolved or suspended to form a liquid dosage form.

Without wishing to be bound by theory, it is believed that the stabilizing effect achieved with the inventive formulations is due to the presence of the antioxidant substance in the final dosage form, and specifically the mixing of the antioxidant with the active ingredient at an early stage of manufacture. Addition of an alditol, a saccharide or both to the active drug/antioxidant mixture may result in a synergistic increase in stability of both the granulation intermediate and the final dosage form. Preferably, processing of the active ingredient should be conducted at temperatures below about 45° C.

Antioxidants are defined herein as compounds which decrease the potential for oxidation of the thyroxine drug. Such antioxidants include, but are not limited to, one or more of the following: butylated hydroxyanisole (BHA), butylated hydroxytoluene (BHT), ascorbic acid, ascorbyl palmitate, propyl gallate, dodecyl gallate, ethyl gallate, octyl gallate, alpha tocopherol, sodium ascorbate, sodium metabisulfite, fumaric acid, malic acid, and any pharmaceutically compatible antioxidant known in the art. Most preferably, the antioxidant of the present invention is butylated hydroxyanisole (BHA).

Alditols which are suitable for use in this invention preferably are those which enhance the stabilizing effect of the antioxidant. Alditols are widely known in the art. Preferred alditols include, but are not limited to, one or more of the following: mannitol, sorbitol, maltitol and xylitol. Most preferably, the alditol is mannitol. Saccharides for use with this invention preferably are those which enhance the stabilizing effect of the antioxidant. Such saccharides include one or more monosaccharides, disaccharides and oligosaccharides composed of 2–10 monosaccharides. Monosaccharides, also known as reducing sugars, which may be used in the present invention generally include aldoses, hemiacetals and cyclic hemiacetals. Disaccharides are generally defined as two monosaccharide units joined together by a glycoside linkage. Oligosaccharides are generally defined as carbohydrates that hydrolyze to yield 2 to 10 molecules of a monosaccharide. Preferred monosaccharides, disaccharides, and oligosaccharides include, but are not limited to: sucrose, maltose, cellobiose, lactose, trehalose, glucose, fructose, galactose, ribose or deoxyribose. Preferably, the saccharide is a monosaccharide or a disaccharide, and more preferably is a disaccharide. The most preferred saccharide is sucrose.

Pharmaceutical compositions of this invention may be prepared for administration orally, rectally, vaginally, transmucosally, transdermally, parenterally, subcutaneously, intramuscularly and intravenously. Pharmaceutically acceptable excipients which are suitable for use in formulations for these methods of administration are known to those of skill in the art and may be included in formulations according to this invention. Generally, excipients contemplated for use in the inventive formulations may include, but are not limited to adjuvants; preservatives; buffers; fillers, extenders, carriers, binders and diluents; glidants and lubricants; surfactants, wetting agents and surface active agents; suspending agents and solvents. Compounds such as dyes and colorants, sweeteners, flavorings, perfuming agents and taste-masking ingredients also may be included in formulations according to this invention. Any pharmaceutically acceptable excipient, such as ingredients to aid in processing or to improve taste or appearance are contemplated for use with these formulations. Further excipients may be included according to the judgment of the pharmaceutical scientist formulating the medicament. In addition, other active ingredients may be included to produce a dual or multiple ingredient medication.

Exemplary surfactants and surface active agents may be selected from known pharmaceutical excipients such as, for example, gelatin, casein, lecithin, gum acacia, stearic acid or other fatty acids, benzalkonium chloride, calcium stearate, glyceryl monostearate or other fatty acid salts, polyethylene glycols, silicon dioxide, methylcelluloses or carboxymethylcelluloses, sodium stearyl fumarate, magnesium stearate, alginate, or any other surface modifying compounds known in the art. Compounds which function as wetting agents, such as, for example, pharmaceutically acceptable detergents and cetyl alcohols also are contemplated for use with the inventive formulations.

Lubricants such as talc, calcium stearate, sodium stearyl fumarate, stearic acid, magnesium stearate, solid polyethylene glycols and cocoa butter are useful with the inventive formulations, as are one or more binders, fillers or extenders such as starches, lactose or other sugars, polyvinylpyrrolidone, sodium citrate, dicalcium phosphate and other alkaline inorganic salts, carboxylmethylcellulose and other cellulose polymers, alginates, gelatins, microcrystalline cellulose, sorbitol, sodium chloride, chitosan, hydrogenated vegetable oil, kaolin, glycerol palmitostearate, magnesium carbonate, and calcium carbonate.

Solid dosage forms which may be prepared according to this invention can include tablets, capsules, rectal or vaginal suppositories, pills, dragees, lozenges, granules, beads, microspheres, pellets and powders, or any combination thereof. Formulations also may be prepared in the form of solutions, suspensions, emulsions, syrups and elixirs. These liquid dosage forms may include liquid diluents in addition to the solid ingredients discussed above. Such diluents may include, but are not limited to solvents, solubilizing agents, suspending agents and emulsifiers such as water or saline solutions, ethanol and other pharmaceutically acceptable alcohols; ethyl carbonate; ethyl acetate; propylene glycol; dimethyl formamide; pharmaceutically acceptable oils such as cottonseed, corn, olive, castor and sesame; fatty acid esters of sorbitan; polyoxyethylene sorbitol; and agar-agar. Formulations can be either immediate or modified release.

The formulations of this invention may be used for any convenient dosage amount of the active ingredient. Generally, the level of the active ingredient may be increased or decreased according to the judgment of the physician, pharmacist, pharmaceutical scientist or other person of skill in the art. The amount of the remaining non-active ingredients can be adjusted as needed. Preferably, the amount of alditol is adjusted to compensate for changes in the amount of active ingredient.

The preferred active ingredient in the formulations of this invention is levothyroxine sodium. Therapeutically effective dosage amounts for this drug generally range from about 0.1 μg to about 5000 μg and are most preferably from about 25 μg to about 300 μg. Exemplary dosages therefore include, but are not limited to 20 μg, 25 μg, 50 μg, 75 μg, 88 μg, 100 μg, 112 μg, 125 μg, 150 μg, 175 μg, 200 μg and 300 μg. Preferred solid dosage forms prepared according to this invention contain the following compounds: levothyroxine sodium (active drug substance); butylated hydroxyanisole (antioxidant); mannitol; microcrystalline cellulose (diluent); polyvinylpyrrolidone (binder); sucrose; crospovidone (disintegrant); magnesium stearate (lubricant); sodium lauryl sulfate (surfactant); and colloidal silicon dioxide (glidant).

Formulations of thyroxine active drugs prepared according to this invention contain about 0.1 μg to about 5000 μg thyroxine active drug substance, preferably about 1 μg to about 1000 μg and most preferably about 25 μg to about 300 μg. Inventive pharmaceutical compositions generally contain by weight about 0.001% to about 2% antioxidant, preferably about 0.005% to about 1% antioxidant and most preferably about 0.01% to about 0.5% antioxidant. Alditols should be present at from about 5% to about 90% (by weight) of the final formulation, preferably from about 15% to about 80% and most preferably from about 25% to about 70%. Filler, such as carbohydrates (starch or cellulose polymer), for example microcrystalline cellulose, generally should comprise from about 5% to about 90% by weight of the final formulations, preferably from about 15% to about 80% and most preferably from about 25% to about 70%. Final dosage forms generally contain from about 5% to about 70% saccharide, by weight, preferably from about 10% to about 60%, and most preferably from about 20% to about 40%. Further optional ingredients in the final dosage form may include a disintegrant, which if present, generally forms from about 2% to about 30% of the final formulation by weight, preferably from about 2% to about 15% and most preferably from about 3% to about 10%. Lubricants may be present in the final formulation at from about 0.1% to about 5% by weight, preferably from about 0.2% to about 3% and most preferably from about 0.5% to about 2.5%. Glidants may be present in final formulations according to this invention at from about 0.05% to about 2% by weight, preferably from about 0.075% to about 1% and most preferably from about 0.1% to about 0.5%. Surfactants may be present in final formulation according to this invention at from about 0.005% to about 1% by weight, preferably from about 0.01% to about 0.5% by weight, and most preferably from about 0.01% to about 0.2%. Binders may be present in final formulation according to this invention at from about 0.1% to about 10% by weight, preferably from about 0.5% to about 5% by weight, and most preferably from about 1% to about 3% by weight.

After the solid ingredients of the formulation are blended, the stabilized drug preparation preferably is compressed into tablets. Alternatively, the preparation may be used to fill capsules such as hard gelatin capsules or used to prepare any other convenient solid dosage form. Compositions according to the invention may be stored in the form of powders, granulates, intermediates, suspensions, or solutions prior to addition of additional desired pharmaceutical excipients for the production of final dosage forms such as tablets or solid-filled capsules, or final liquid dosage forms such as solutions, syrups, suspensions, emulsions and the like.

The following example further illustrates the invention and is not to be construed to limit the claims in any manner.

EXAMPLE 1

TABLE 1

Levothyroxine 25 mcg tablets were prepared using the following ingredients.

| 0.0334% Levothyroxine Sodium Granulation Intermediate | |
|---|---|
| Levothyroxine Sodium | 567.2 mg |
| Mannitol | 723.0 g |
| Sucrose | 425.0 g |
| Microcrystalline Cellulose | 517.0 g |
| Polyvinylpyrrolidone K30 | 34.0 g |
| Butylated Hydroxyanisole | 340 mg |
| Purified Water | 165.0 g |
| Ethanol 200 proof | 29.0 g |
| Levothyroxine Sodium 25 mcg Tablets | |
| 0.0334% Levothyroxine Sodium Granulation Intermediate | 1125 g |
| Colloidal Silicon Dioxide | 5.3 g |
| Magnesium Stearate/Sodium Lauryl Sulfate 94/6 | 30.0 g |
| FD&C Yellow Aluminum Lake No. 6 | 4.5 g |
| Microcrystalline Cellulose | 136.5 g |
| Mannitol | 648.8 g |

The mannitol and the levothyroxine sodium were blended for 10 minutes using conventional mixing equipment. The blended material, microcrystalline cellulose, and the sucrose were then passed through a hammer mill and the milled materials were blended for 15 minutes. With continuous mixing, the powders were granulated with a 15% w/w hydroalcoholic solution of polyvinylpyrrolidone and butylated hydroxyanisole. Additional water was added as needed for consistency of the granulation. The wet granulation mixture was dried in a fluidized bed dryer at 40° C. until the moisture content was less then 4%. The dried granulation was sized by passing it through a hammer mill then blended for 5 minutes using conventional mixing equipment.

The colloidal silicon dioxide, the magnesium stearate/sodium lauryl sulfate (94/6), and the FD&C Yellow Aluminum Lake No. 6 lake were blended for 3 minutes and the mixture was passed through a #30 mesh screen. The microcrystalline cellulose and the mannitol were sized by screening and milling, respectively. The screened ingredients were then blended with the levothyroxine sodium granulation intermediate for 15 minutes until uniform. The mixture was compressed into tablets, each weighing approximately 130 mg, on a rotary tableting machine.

These tablets were tested for stability against tablets prepared with the same formulation as above but lacking antioxidant. FIG. 1 graphically represents the stability data. The tablets were stored at 25, 40, 50 and 60° C. for 5 days at ambient humidity in 75 cc standard HDPE pharmaceutical containers. Samples of these tablets were analyzed for impurity levels using an HPLC standard assay. Evaluation of the impurity profiles for these tablets demonstrates that the antioxidant stabilized formulation yields an impurity profile with a lower overall total impurities content at all temperatures compared to tablets lacking antioxidant, especially at high temperatures in contrast to the predicted behavior. Total impurities include liothyronine and other known and unknown impurities.

The invention claimed is:

1. A storage stable pharmaceutical composition in unit dosage form which comprises a therapeutically effective amount of a thyroxine active drug, an amount of an antioxidant sufficient to inhibit oxidative degradation of said drug, a stabilizing amount of an alditol which is from about 5% to about 90% of the total weight of said composition, a stabilizing amount of a saccharide which is from about 20% to about 40% of the total weight of said composition, and optionally further comprises other pharmaceutically acceptable excipients wherein said antioxidant is selected from the group consisting of butylated hydroxyanisole, butylated hydroxytoluene, propyl gallate, dodecyl gallate, ethyl gallate, octyl gallate, sodium metabisulfite, fumaric acid and malic acid.

2. A composition of claim 1 wherein said thyroxine active drug is levothyroxine sodium.

3. A composition of claim 1 wherein said amount of antioxidant sufficient to inhibit oxidative degradation of said drug is from about 0.001% to about 2% of the total weight of said composition.

4. A composition of claim 1 wherein said amount of antioxidant sufficient to inhibit oxidative degradation of said drug is from about 0.005% to about 1% of the total weight of said composition and wherein said stabilizing amount of alditol is from about 15% to about 80% of the total weight of said composition.

5. A composition of claim 1 wherein said amount of antioxidant sufficient to inhibit oxidative degradation of said drug is from about 0.01% to about 0.5% of the total weight of said composition and wherein said stabilizing amount of alditol is from about 25% to about 70% of the total weight of said composition.

6. A composition of claim 1 wherein said antioxidant is butylated hydroxyanisole.

7. A composition of claim 1, wherein said alditol is selected from the group consisting of mannitol, sorbitol, maltitol and xylitol.

8. A composition of claim 1 wherein said alditol is mannitol.

9. A composition of claim 1, wherein said saccharide is selected from the group consisting of sucrose, maltose, cellobiose, lactose, trehalose, glucose, fructose, ribose and deoxyribose.

10. A composition of claim 9, wherein said saccharide is sucrose.

11. A storage stable oral pharmaceutical composition in unit dosage form which comprises a therapeutically effective amount of levothyroxine sodium, an amount of butylated hydroxyanisole sufficient to inhibit oxidative degradation of said drug which is from about 0.001% to about 2% of the total weight of said composition, a stabilizing amount of mannitol which is from about 5% to about 90% of the total weight of said composition, a stabilizing amount of sucrose which is from about 20% to about 40% of the total weight of said composition, and optionally further comprises other pharmaceutically acceptable excipients.

12. A composition of claim 11 wherein said amount of butylated hydroxyanisole sufficient to inhibit oxidative degradation of said drug is from about 0.005% to about 1% of the total weight of said composition and wherein said stabilizing amount of mannitol is from about 15% to about 80% of the total weight of said composition.

13. A composition of claim 11 wherein said amount of butylated hydroxyanisole sufficient to inhibit oxidative degradation of said drug is from about 0.01% to about 0.5% of the total weight of said composition and wherein said stabilizing amount of mannitol is from about 25% to about 70% of the total weight of said composition.

14. A storage stable oral pharmaceutical composition in unit dosage form which comprises a therapeutically effective amount of levothyroxine sodium, butylated hydroxyanisole in an amount of about 0.001% to about 2% of the total weight of said composition, mannitol in an amount of about 5% to about 90% of the total weight of said composition, sucrose in an amount of about 20% to about 40% of the total weight of said composition, and optionally further comprises microcrystalline cellulose, polyvinylpyrrolidone, crospovidone, magnesium stearate, sodium lauryl sulfate, and colloidal silicon dioxide.

15. A storage stable oral pharmaceutical composition in unit dosage form which comprises:
   (a) a therapeutically effective amount of levothyroxine sodium;
   (b) about 0.01% by weight butylated hydroxyanisole;
   (c) about 39% by weight mannitol;
   (d) about 23% by weight sucrose;
   (e) about 28% by weight microcrystalline cellulose;
   (f) about 1.5% by weight polyvinylpyrrolidone;
   (g) about 6% by weight crospovidone;
   (h) about 2% by weight magnesium stearate;
   (I) about 0.3% by weight colloidal silicon dioxide; and
   (j) about 0.1% by weight sodium lauryl sulfate.

16. A method for the treatment of thyroid disorders comprising orally administering the composition of claim 1 to a human.

17. A method for the treatment of thyroid disorders comprising orally administering the composition of claim 15 to a human.

18. A composition of claim 1 which is a solid oral dosage form.

19. A composition of claim 15 which is a solid oral dosage form.

20. A composition of claim 1 which is a tablet.

21. A composition of claim 15 which is a tablet.

* * * * *